United States Patent
Quan et al.

(10) Patent No.: US 9,539,418 B2
(45) Date of Patent: Jan. 10, 2017

(54) PROTEOGLYCAN-CONTAINING MICRONEEDLE ARRAY

(75) Inventors: Ying-shu Quan, Kyoto (JP); Fumio Kamiyama, Kyoto (JP); Takao Taki, Osaka (JP); Kazuyoshi Kawai, Osaka (JP); Tadayoshi Takemoto, Osaka (JP); Takuya Hamabuchi, Osaka (JP); Kazuhide Ohta, Osaka (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 539 days.

(21) Appl. No.: 13/635,813

(22) PCT Filed: Mar. 18, 2011

(86) PCT No.: PCT/JP2011/056643
§ 371 (c)(1),
(2), (4) Date: Sep. 18, 2012

(87) PCT Pub. No.: WO2011/115272
PCT Pub. Date: Sep. 22, 2011

(65) Prior Publication Data
US 2013/0012882 A1    Jan. 10, 2013

(30) Foreign Application Priority Data
Mar. 19, 2010   (JP) .................................. 2010-065089

(51) Int. Cl.
*A61M 37/00* (2006.01)
*A61K 9/00* (2006.01)
(Continued)

(52) U.S. Cl.
CPC .......... *A61M 37/0015* (2013.01); *A61K 8/981* (2013.01); *A61K 8/987* (2013.01);
(Continued)

(58) Field of Classification Search
CPC ................. A61M 37/0015; A61M 2037/0023; A61M 2037/0046; A61M 2037/0053; A61M 2037/003
(Continued)

(56) References Cited

U.S. PATENT DOCUMENTS

2002/0138049 A1*  9/2002 Allen et al. .................... 604/272
2004/0180106 A1*  9/2004 Theoharides ................. 424/769
(Continued)

FOREIGN PATENT DOCUMENTS

EP      1 270 599 A1    1/2003
EP      1 475 392 A1    11/2004
(Continued)

OTHER PUBLICATIONS

Supplementary European Search Report dated Sep. 5, 2013 for EP Application No. 11756455.9.
(Continued)

*Primary Examiner* — Imani Hayman
*Assistant Examiner* — Nilay Shah
(74) *Attorney, Agent, or Firm* — Sughrue Mion, PLLC

(57) ABSTRACT

A microneedle array is provided which has (1) the strength to withstand insertion into the skin surface layer and/or stratum corneum, (2) the fineness and flexibility to cause no pain or bleeding in the skin surface layer and/or stratum corneum at the insertion site of the microneedles, and (3) solubility or biodegradability of the microneedle portions under the skin. The microneedle array is produced by forming microneedles using proteoglycan as a base material.

6 Claims, 4 Drawing Sheets

(51) Int. Cl.
*A61Q 19/00* (2006.01)
*A61Q 19/08* (2006.01)
*A61K 8/98* (2006.01)

(52) U.S. Cl.
CPC ............ *A61K 9/0021* (2013.01); *A61Q 19/00* (2013.01); *A61Q 19/08* (2013.01); *A61K 2800/87* (2013.01); *A61K 2800/91* (2013.01); *A61M 2037/0023* (2013.01); *A61M 2037/0046* (2013.01); *A61M 2037/0053* (2013.01)

(58) Field of Classification Search
USPC .................................................. 604/173, 272
See application file for complete search history.

(56) References Cited

U.S. PATENT DOCUMENTS

| | | | |
|---|---|---|---|
| 2008/0004238 A1 | 1/2008 | Marcum et al. | |
| 2008/0208134 A1* | 8/2008 | Tomono | 604/173 |
| 2009/0182306 A1* | 7/2009 | Lee et al. | 604/506 |
| 2010/0114348 A1* | 5/2010 | Boyden et al. | 700/97 |
| 2011/0028905 A1 | 2/2011 | Takada | |
| 2011/0112509 A1 | 5/2011 | Nozaki et al. | |

FOREIGN PATENT DOCUMENTS

| | | |
|---|---|---|
| EP | 1 844 763 A1 | 10/2007 |
| EP | 1 935 438 A1 | 6/2008 |
| EP | 1 985 623 A1 | 10/2008 |
| EP | 2 213 284 A1 | 8/2010 |
| EP | 2 283 809 A1 | 2/2011 |
| EP | 2 327 419 A1 | 6/2011 |
| EP | 2 338 557 A1 | 6/2011 |
| JP | 2003-300858 A | 10/2003 |
| JP | 2007-131548 A | 5/2007 |
| JP | 2009-173702 A | 8/2009 |
| JP | 2009-201956 A | 9/2009 |
| JP | 2009-254756 A | 11/2009 |
| JP | 2009-273872 A | 11/2009 |
| WO | 2009/066763 A1 | 5/2009 |
| WO | WO 2009120995 A2 * | 10/2009 |
| WO | 2010/001671 A1 | 1/2010 |

OTHER PUBLICATIONS

Hideto Watanabe et al., "Roles of Aggrecan, a Large Chondroitin Sulfate Proteoglycan, in Cartilage Structure and Function", J. Biochem., 1998, pp. 687-693, vol. 124, No. 4.

Sakae Ota et al., "Effects of Proteoglycan on Dextran Sulfate Sodium-Induced Experimental Colitis in Rats", Dig Dis Sci, 2008, pp. 3176-3183, vol. 53, No. 12.

Toshihito Mitsui et al., "Salmon cartilage proteoglycan suppresses mouse experimental colitis through induction of Foxp3 regulatory T cells", Biochemical and Biophysical Research Communications, 2010, pp. 209-215, vol. 402, No. 2.

Hiroshi Sashinami et al., "Salmon cartilage proteoglycan modulates cytokine responses to *Escherichia coli* in mouse macrophages", Biochemical and Biophysical Research Communications, 2006, pp. 1005-1010, vol. 351, No. 4.

International Search Report dated May 24, 2011 for PCT/JP2011/056643.

* cited by examiner

PROTEOGLYCAN-CONTAINING MICRONEEDLE ARRAY

CROSS REFERENCE TO RELATED APPLICATIONS

This application is a National Stage of International Application No. PCT/JP2011/056643 filed Mar. 18, 2011, claiming priority based on Japanese Patent Application No. 2010065089 filed Mar. 19, 2010, the contents of all of which are incorporated herein by reference in their entirety.

TECHNICAL FIELD

The present invention relates to a microneedle array that can be used as an external preparation. More specifically, the present invention relates to a microneedle array that is cosmetically or pharmaceutically effective.

PRIOR ART

External preparations containing medicinal components are conventionally used so that the medicinal components may exhibit pharmacological activity under the skin. Solutions, ointments, cream preparations, tape preparations, patches, poultices, etc., are known as such external preparations. These are topically applied or attached, so that medicinal components are percutaneously absorbed to thereby exhibit desired pharmacological activity under the skin.

However, such external preparations in an applied or attached form have drawbacks, i.e, they might be removed or lost due to sweating, washing, external pressure, and other factors while in use before the medicinal components are percutaneously absorbed. Another problem of these external preparations is that the medicinal components are not percutaneously absorbed to a sufficient degree because of the barrier function of the skin, and hence they fail to exhibit the desired pharmacological activity. Particularly, when polymer compounds are used as medicinal components, percutaneous absorption is difficult, thus making it difficult for the external preparations to exhibit the desired pharmacological activity.

Recently, as a technique for solving these drawbacks of external preparations, microneedle arrays having microneedles comprising medicinal components are being actively studied (Patent Documents 1, to 3). For example, Patent Document 1, proposes a microneedle array having microneedles formed of a raw material mainly composed of collagen. According to the microneedle array of Patent Document 1, the microneedles are inserted into the skin surface layer and/or stratum corneum to supply the medicinal components contained in the microneedles under the skin. The inserted portions of the microneedles can dissolve or biodegrade under the skin and thus disappear. Further, when the microneedles of Patent Document 1, which have very fine needle parts, are inserted into the skin surface layer and/or stratum corneum, neither pain nor bleeding occurs, and puncture wounds close quickly. The microneedles of Patent Document 1, are thus suitable for supplying medicinal components under the skin.

At the same time, microneedle arrays are required to have optimal designs depending on skin diseases or skin conditions. There is thus a demand for various kinds of microneedle arrays. However, the microneedles of microneedle arrays used as external preparations are required to comprehensively have the following properties: (1) the strength to withstand insertion into the skin surface layer and/or stratum corneum, (2) the fineness and flexibility to cause no pain or bleeding in the skin surface layer and/or stratum corneum at the insertion site of the microneedles, and (3) solubility or biodegradability in the body of the microneedle portions under the skin. Accordingly, it is very difficult to change the design of the constituent materials of microneedle arrays, and this is particularly true for the main constituent material of the microneedles. For these reasons, only a few constituent materials for microneedle arrays have been reported at present.

In recent years, medical or cosmetic applications of proteoglycan have attracted attention. Proteoglycan is known as a glycoconjugate composed of a core protein and glycosaminoglycan (acid mucopolysaccharide) bonded thereto. Proteoglycan is the principal constituent of the extracellular matrix, and is present in skin tissue, cartilage tissue, bone tissue, vascular tissue, etc. Proteoglycan is reportedly involved with the growth and bonding of subcutaneous cells. Moreover, proteoglycan is reportedly useful in preventing or treating inflammatory diseases or autoimmune diseases, preventing rejection after organ transplantation, preventing or improving allergies, and preventing or improving diabetes (see Patent Document 4).

However, using proteoglycan in microneedle arrays has not been studied. At present, there is no clue as to whether proteoglycan can be used to form microneedles.

PRIOR ART DOCUMENTS

[Patent Documents]

Patent Document 1: Japanese Unexamined Patent Publication No. 2009-273872

Patent Document 2: Japanese Unexamined Patent Publication No. 2009-254756

Patent Document 3: Japanese Unexamined Patent Publication No. 2009-201956

Patent Document 4: Japanese Unexamined Patent Publication No. 2007-131548

Patent Document 5: Japanese Unexamined Patent Publication No. 2003-300858

[Non-Patent Document]

Non-Patent Document 1:, Watanabe H, Yamada Y, Kimata K., Roles of aggrecan, a large chondroitin sulfate proteoglycan, in cartilage structure and function.; J Biochem. 1998 Oct;124(4):687-93.

Non-Patent Document 2:, Ota S, Yoshihara S, Ishido K, Tanaka M, Takagaki K, Sasaki M., Effects of proteoglycan on dextran sulfate sodium-induced experimental colitis in rats. Ota S; Dig Dis Sci. 2008, Dec;53(12):3176-83. Epub 2008, May 8.

Non-Patent Document 3:, Mitsui T, Sashinami H, Sato F, Kijima H, Ishiguro Y, Fukuda S, Yoshihara S, Hakamada K, Nakane A, Salmon cartilage proteoglycan suppresses mouse experimental colitis through induction of Foxp3+ , regulatory T cells.; Biochem Biophys Res Commun. 2010, Nov 12;402(2):209-15. Epub 2010, Oct 20.

Non-Patent Document 4:, Sashinami H, Takagaki K, Nakane A., Salmon cartilage proteoglycan modulates cytokine responses to Escherichia coli in mouse macrophages.; Biochem Biophys Res Commun. 2006, Dec 29;351 (4):1005-10. Epub 2006, Nov 3.

SUMMARY OF THE INVENTION

[Problem to Be Solved by the Invention]

An object of the present invention is to provide a novel and unprecedented microneedle array. More specifically, an object of the present invention is to provide a novel microneedle array comprising one or more microneedles that have the following properties:

(1) the strength to withstand insertion into the skin surface layer and/or stratum corneum, (2) the fineness and flexibility to cause no pain or bleeding in the skin surface layer and/or stratum corneum at the insertion site of the microneedles, and (3) solubility or biodegradability in the body of the microneedle portions under the skin.

[Means for Solving the Problem]

The present inventors conducted extensive studies to solve the above problems, and surprisingly found that proteoglycan can be used as a base material to form microneedles, and that a microneedle array having the microneedles can be produced. The present inventors also found that the microneedle array has the excellent properties described above in items (1) to (3), and is highly useful as an external preparation. Additionally, the microneedle array is expected to effectively exhibit proteoglycan-based useful pharmacological activity under the skin.

The present invention was accomplished by conducting further studies based on these findings.

More specifically, the present invention provides a microneedle array and a production method thereof according to the following embodiments:

(I) Microneedle Array (I-1). A microneedle array comprising one or more microneedles formed on the surface of a substrate, the microneedles containing proteoglycan as a base material.

(I-2). The microneedle array according to (I-1), wherein each of the microneedles has a konide-like shape or a circular truncated cone shape.

(I-3). The microneedle array according to (I-1) or (I-2), wherein each of the microneedles is a solid needle.

(I-4). The microneedle array according to any one of (I-1) to (I-3), wherein each of the microneedles has a root diameter of 120, to 400, pm, a tip diameter of 5, to 100, μm, and a length of 100, to 5000, μm, and the pitch (the distance from tip to tip) between adjacent microneedles is 100, to 1800, μm.

(I-5). The microneedle array according to (I-4), wherein each of the microneedles has a length of 100, to 1600, pm or 100, to 1000, μm.

(I-6). The microneedle array according to (I-4), wherein each of the microneedles has a length of more than 1000, μm but not more than 5000, μm, or more than 1000, μm but not more than 3000 μm.

(I-7). The microneedle array according to (I-4), wherein each of the microneedles has a length of more than 1600, μm but not more than 5000, μm, or more than 1600, μm but not more than 3000 μm.

The microneedle arrays shown in the (I-6) and (I-7) comprise the needles having a millimeter -order length as above mentioned, but a micrometer-order fineness (the root diameter and the tip diameter of needle). The microneedle array of the present invention includes such arrays having the above needles having a millimeter-order length and a micrometer-order fineness.

(I-8). The microneedle array according to any one of (I-1) to (I-7), wherein the proteoglycan content in the one or more microneedles is 20, to 100, wt. %.

(I-9). The microneedle array according to any one of (I-1) to (I-8), wherein the proteoglycan is chondroitin sulfate proteoglycan.

(I-10). The microneedle array according to any one of (I-1) to (I-9), wherein the proteoglycan is derived from fish.

(I-11). The microneedle array according to (I-10), wherein the fish is salmon, shark or jellyfish.

(I-12). The microneedle array according to any one of (I-1) to (I-11), wherein the one or more microneedles contain, in addition to the proteoglycan, a water-soluble polymer other than proteoglycan, or a cosmetically or pharmaceutically acceptable medicinal component.

(I-13). The microneedle array according to any one of (I-1) to (I-12), wherein the substrate has the same composition as the microneedles.

(II) Method of Producing Microneedle Array (II-1). A method of producing the microneedle array according to (I-1) or (I-11), the method comprising the steps of:

pouring an aqueous solution in which proteoglycan for forming microneedles is dissolved into a mold in which the form of a microneedle array is recessed, so that a microneedle part and a substrate part are formed;

evaporating the moisture to dryness at room temperature or by heating; and removing the formed microneedle array from the mold.

(II-2). A method of producing the microneedle array according to (I-1), the method comprising the steps of:

pouring an aqueous solution in which proteoglycan for forming microneedles is dissolved into a mold in which the form of a microneedle is recessed;

evaporating the moisture to dryness at room temperature or by heating;

laminating a substrate thereon and combining or bonding the bottom of the microneedles and the substrate; and removing the microneedles combined or bonded with the substrate from the mold.

(II-3). The method according to (II-1) or (II-2), wherein the aqueous solution in which proteoglycan for forming microneedles is dissolved contains the proteoglycan at a concentration of about 1, to 30, wt. %, preferably about 1, to 25, wt. %.

[Effect of the Invention]

The present invention provides a microneedle array having one or more microneedles formed using proteoglycan as a base material. The microneedle array of the present invention comprises one or more microneedles that have the above excellent properties, i.e., (1) strength, (2) fineness and flexibility, and (3) solubility in the body. The microneedle array, which thus has sufficient properties for use as an external preparation, can adequately supply proteoglycan under the skin and underlying tissues.

Moreover, the microneedle array of the present invention is suitable for cosmetic or medical applications using the action of proteoglycan. Particularly, the microneedle array of the present invention is expected to an anti-aging activity such as a wrinkle-smoothing effect based on the epidermal cell growth-promoting activity of proteoglycan.

BRIEF DESCRIPTION OF THE DRAWINGS

FIG. 3 shows a perspective view and an image of the microneedle array of the present invention used in Example 2.

FIG. 4 shows the results of Example 2.

MODE FOR CARRYING OUT THE INVENTION

Figure 1:
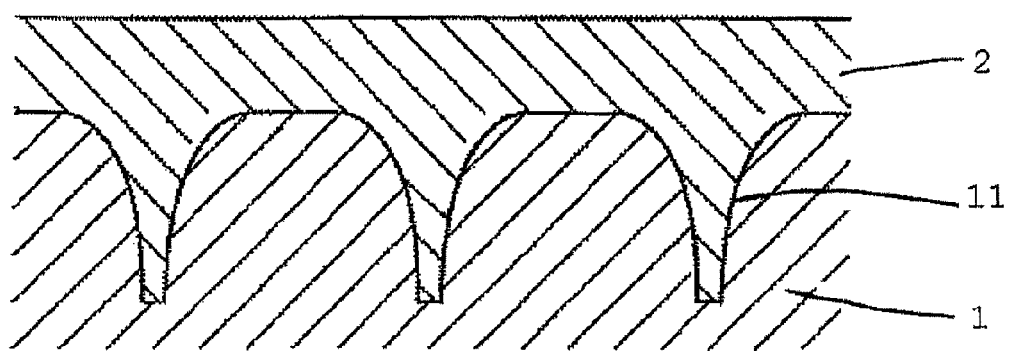
FIG. 1 shows a cross-sectional view of a mold (1) having microneedle-like shape recesses (11) and filled with a proteoglycan-containing aqueous solution (2).

The microneedle array of the present invention comprises one or more microneedles formed on the surface of a substrate, the microneedles containing proteoglycan as a base material. The following describes the microneedle array of the present invention in detail.

Proteoglycan is a general term for molecules in which one or more glycosaminoglycans are covalently linked to a core protein. The type of proteoglycan used in the present invention is not particularly limited, and any of those belonging to chondroitin sulfate proteoglycan, dermatan sulfate proteoglycan, heparan sulfate proteoglycan, and keratan sulfate proteoglycan can be used.

Specific examples of proteoglycan used in the present invention include aggrecan, versican, neurocan, brevican, decorin, biglycan, serglycin, perlecan, syndecan, glypican, lumican, keratocan, etc. Among these, it is preferable, in the present invention, to use chondroitin sulfate proteoglycan, and more preferably aggrecan, as a base material for forming microneedles.

The source of proteoglycan used in the present invention is not particularly limited, and any of those derived from mammals such as humans, cows, and pigs; birds such as chickens; fish such as sharks, salmon and jellyfish; shellfish such as crabs and shrimps; and the like can be used. Among these sources, it is preferable to use proteoglycan derived from fish, more preferably salmon, and particularly preferably salmon nasal cartilage.

Compared with proteoglycan derived from cows, pigs, and other higher animals, proteoglycan derived from shark cartilage has higher transparency, and is effective as a starting material for external skin preparations. For the purpose of reducing dark spots, wrinkles, and sagging, it is known to combine shark cartilage-derived proteoglycan with a melanogenesis inhibitor and a crude drug extract having an active oxygen eliminating effect (Patent Document 5).

The molecular weight of proteoglycan used in the present invention is not particularly limited, and is suitably determined. Proteoglycan having a molecular weight of 80,000, to 3000,000, can generally be used without limitation; preferably used is proteoglycan having a molecular weight of 200,000, to 2500,000,, and more preferably 300,000, to 800,000.

In the present invention, the proportion of proteoglycan in the microneedles is not particularly limited as long as the microneedles contain proteoglycan as a base material. For example, the amount of proteoglycan in the microneedles is generally 20, to 100 wt. %, preferably 50, to 100, wt. %, more preferably 70, to 100 wt. %, even more preferably 80, to 100, wt. %, and still more preferably 90, to 100, wt. %.

More specifically, the microneedles of the present invention comprising proteoglycan as a base material may be composed only of proteoglycan, or may contain components other than proteoglycan in an amount up to 80, wt. %, and preferably 50, wt. %, as long as the following properties of the microneedles composed of proteoglycan are not impaired:

(1) the strength to withstand insertion into the skin surface layer and/or stratum corneum, (2) the fineness and flexibility to cause no pain or bleeding in the skin surface layer and/or stratum corneum at the insertion site of the microneedles, and (3) solubility or biodegradability in the body of the microneedle portions under the skin.

In the present invention, "comprising proteoglycan as a base material" indicates the above meaning.

As components other than proteoglycan containable in the microneedles, water-soluble polymers other than proteoglycan can be used. Such water-soluble polymers may be those that can dissolve or degrade in vivo, and specific examples thereof include polysaccharides such as hyaluronic acid, chondroitin sulfate, glycogen, dextrin, dextran, dextran sulfate, hydroxypropyl methylcellulose, alginic acid, chitin, chitosan, and pullulan; proteins such as collagen, gelatin, and hydrolysates thereof; synthetic high polymers such as polyvinyl alcohol, polyvinyl pyrrolidone, polyacrylic acid, and carboxyvinyl polymer; and the like.

When the microneedles contain a water-soluble polymer other than proteoglycan, the amount of the water-soluble polymer in the microneedles is generally 1, to 30 wt. %, preferably 1, to 25, wt. %, more preferably 1, to 20 wt. %, and further more preferably 1, to 10, wt. %.

Moreover, in the present invention, the microneedles may contain cosmetically or pharmaceutically acceptable medicinal components as the above other components.

Among such medicinal components, examples of cosmetically acceptable medicinal components include whitening agents such as ascorbic acid, sodium ascorbyl phosphate, magnesium ascorbyl phosphate, ascorbyl palmitate, kojic acid, rucinol, tranexamic acid, licorice extract, and vitamin-A derivatives; anti-wrinkle agents such as retinol, retinoic acid, retinol acetate, and retinol palmitate; blood circulation accelerators such as tocopheryl acetate, capsaicin, and nonylic acid vanillylamide; dietary agents such as raspberry ketone, evening primrose extract, and seaweed extract; antimicrobial agents such as isopropyl methyl phenol, photosensitive pigments, and zinc oxide; antiphlogistics such as salicylic acid; vitamins such as vitamin D2, vitamin D3, and vitamin K; and the like.

Further, among the above medicinal components, pharmaceutically acceptable medicinal components may be, other than the cosmetically acceptable medicinal components described above, medicines used in the pharmaceutical field. Specific examples of medicines other than the aforementioned cosmetically available medicinal components include antipyretic analgesic antiphlogistics, such as ibuprofen, flurbiprofen, and ketoprofen; steroidal anti-inflammatory agents, such as hydrocortisone, triamcinolone, and prednisolone; vasodilators, such as diltiazem hydrochloride and isosorbide nitrate; antiarrhythmic agents, such as procainamide hydrochloride and mexiletine hydrochloride; antihypertensives, such as clonidine hydrochloride, bunitrolol hydrochloride, and captopril; local anesthetics, such as tetracaine hydrochloride and propitocaine hydrochloride; hormone drugs, such as propylthiouracil, estradiol, estriol, and progesterone; antihistamines, such as diphenhydramine hydrochloride and chlorpheniramine maleate; anesthetics, such as pentobarbital sodium; soporific analgesics, such as amobarbital and phenobarbital; antiepileptic agents, such as phenytoin sodium; antipsychotic drugs, such as chlorpromazine hydrochloride, imipramine hydrochloride, chlordiazepoxide, and diazepam; skeletal muscle relaxants, such as suxamethonium hydrochloride and eperisone hydrochloride; autonomic drugs, such as neostigmine bromide and bethanechol chloride; antiparkinson agents, such as amantadine hydrochloride; diuretics, such as hydroflumethiazide, isosorbide, and furosemide; vasoconstrictors, such as phenylephrine hydrochloride; respiratory stimulants, such as lobeline hydrochloride, dimorpholamine, and naloxone hydrochloride; narcotics, such as morphine hydrochloride, cocaine hydrochloride, and pethidine hydrochloride; and the like. Furthermore, in the present invention, medicines to be added to the microneedles may be, other than those exemplified above, biologically active peptides and derivatives thereof, and fragments of nucleic acids, oligonucleotides, antigen proteins, bacteria, viruses, etc. Examples of such biologically active peptides and derivatives thereof include calcitonin, adrenocorticotropic hormone, parathyroid hormone (PTH), hPTH (1→34), insulin, secretin, oxytocin, angiotensin, β-endorphin, glucagon, vasopressin, somatostatin, gastrin, luteinizing hormone-releasing hormone, enkephalin, neurotensin, atrial natriuretic peptide, growth hormone, growth hormone-releasing hormone, bradykinin, substance P, dynorphin, thyrotropic hormone, prolactin, interferon, interleukin, G-CSF, glutathione peroxidase, superoxide dismutase, desmopressin, somatomedin, endothelin, salts thereof, etc. Examples of the above antigen protein include HBs surface antigen, HBe antigen, etc.

The microneedle array of the present invention has a structure in which one or more microneedles are formed on the surface of a substrate. In the microneedle array of the present invention, the larger the number of microneedles, the higher the desired pharmacological activity. Accordingly, the substrate is desirably provided with a plurality of microneedles.

Figure 2:
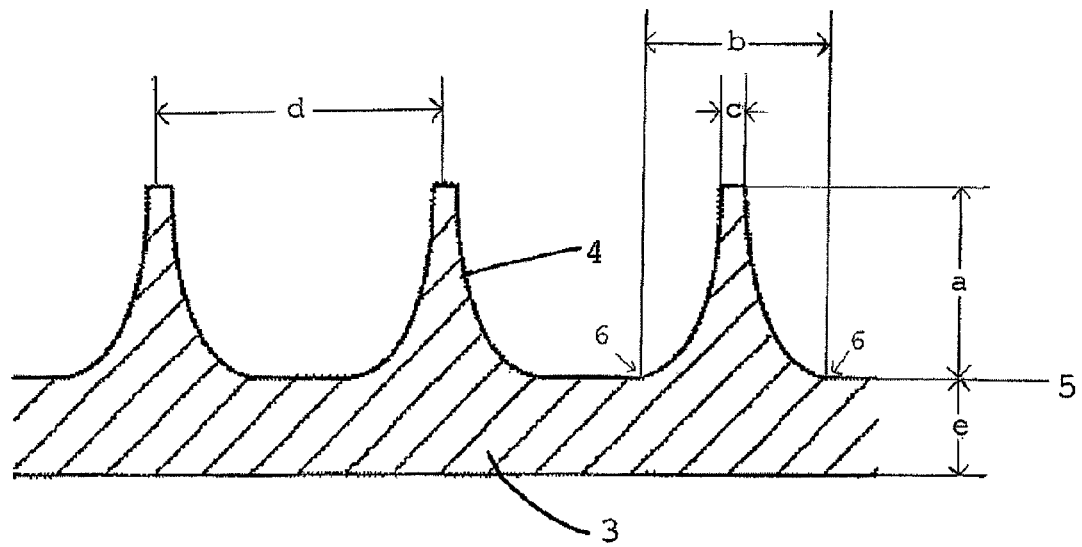
FIG. 2 shows a cross-sectional view of an example of the microneedle array of the present invention (Example 1). The microneedle array has a structure in which a plurality of solid konide-like shape microneedles (4) are formed on the surface of a substrate (3). In the drawing, Sign "a" denotes the length (height) of the microneedle formed on the substrate; Sign "b" denotes the root diameter of the microneedle; Sign "c" denotes the tip diameter of the microneedle; Sign "d" denotes the distance (pitch) between tips of adjacent microneedles formed on the substrate; and Sign "e" denotes the thickness of the substrate. Here, the "root diameter" of the microneedle indicates the diameter of the bottom of the microneedle attached to the surface of the substrate. More specifically, in the cross-sectional view shown in FIG. 2, the "root diameter" corresponds to the distance between the tangent points (6) of the microneedle relative to the substrate surface (5), which is regarded as the base line.
Figure 3A:
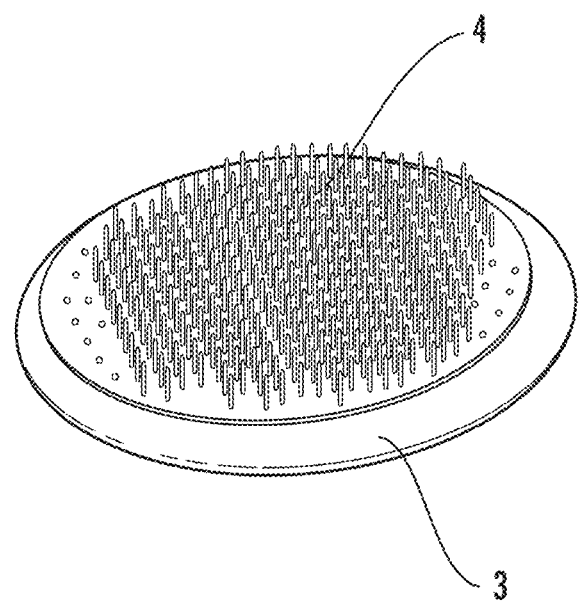
FIG. 3A illustrates a perspective view and FIG. 3B shows the microneedle array before use.
Figure 3B:
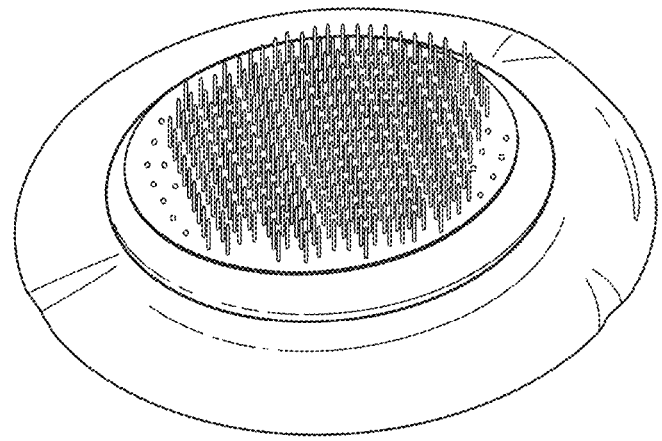
Figure 3C:
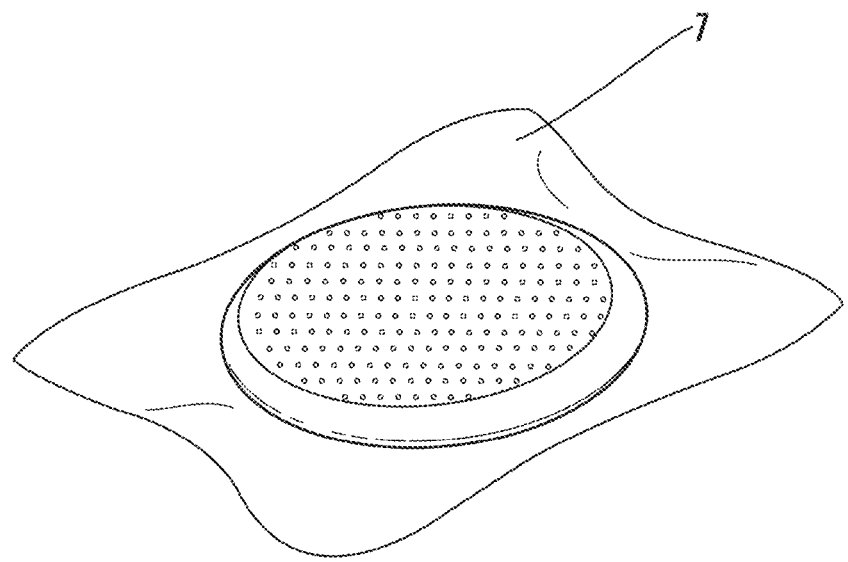
FIG. 3C illustrates a perspective view and FIG. 3D shows the microneedle array after use. Sign "7" denotes a tape used to fix the microneedle array to the skin of the knee.
Figure 3D:
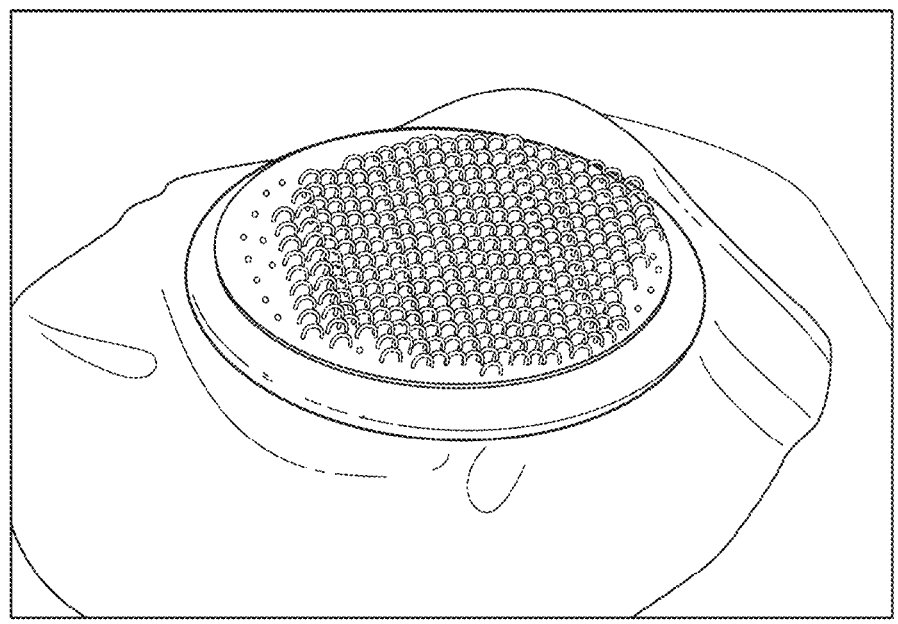
Figure 4A:
FIG. 4A is an image of a site to which the microneedle array of the present invention containing a dye has been applied and then removed.
Figure 4B:
FIG. 4B is an image of the subcutaneous tissue of the site to which the microneedle array has been applied.

The form of the microneedle may be suitably determined so that it can be inserted into the skin and dissolve in the body (in the skin and underlying tissue), and so that pain and bleeding do not occur. For example, the microneedle preferably has a konide-like shape, a circular truncated cone shape, or the like. The konide-like shape as used herein is a so-called volcano shape, that is, a circular truncated cone whose side surface is internally curved, as shown in FIG. 2. Moreover, the microneedle is preferably a solid needle, rather than a hollow needle.

A microneedle in a konide-like shape or a circular truncated cone shape preferably has a root diameter of about 120, to 400 μ, m, and more preferably about 150, to 300 μm, because a thin microneedle supplies a smaller amount of proteoglycan into the skin, and is easily broken when inserted into the skin, whereas a thick microneedle is hard to insert into the skin. The "root diameter" of the microneedle indicates the diameter of the bottom of the microneedle attached to the surface of the substrate.

A microneedle in a konide-like shape or a circular truncated cone shape preferably has a tip diameter of about 5, to 100 μ, m, and more preferably about 10, to 80 μ, m, because a thin (sharp) microneedle is easily broken when inserted into the skin, whereas a thick microneedle is hard to insert into the skin, thereby causing pain.

A microneedle in a konide-like shape or a circular truncated cone shape preferably has a length of about 100 μ, m or more, preferably about 150 μ, m or more, and more preferably about 200 μ, m or more, because a short microneedle is shallowly inserted into the skin and therefore makes it difficult to supply proteoglycan. The upper limit of the length of the microneedle is not particularly limited as long as the microneedle is not broken when inserted into the skin. The upper limit of the length is generally about 5000 μ, m or less, preferably about 3000 μ, m or less, and more preferably about 1600 μ, m or les. Specifically, the length of the microneedle is, for example, about 100, to 5000 μ, m, preferably about 100, to 3000 μ, m. The microneedle is included the microneedle having a length of about 100, to 1600 μ, m, preferably about 150, to 1200 μ, m, or more preferably about 150, to 1000 μ, m, and the microneedle having a length of more than about 1000 μ, m but not more than 5000 μ, m, preferably more than about 1600 μ, m but not more than 5000 μ, m, or more preferably more than about 1600 μ, m but not more than 3000 μm.

In the microneedle array, as for the distance between one microneedle and an adjacent microneedle, a shorter distance makes it difficult to insert the microneedles into the skin, while a longer distance results in a smaller number of microneedles per unit area, causing an insufficient supply of proteoglycan into the skin. From this viewpoint, the space between the microneedles arranged in the microneedle array is preferably such that the distance between the tip of one microneedle and the tip of an adjacent microneedle (this distance is referred to as the "pitch" in the present invention) is about 100, to 1800 μ, m, and preferably about 150, to 1200 μ, m.

The number of microneedles per unit area of the substrate surface of the microneedle array is suitably determined depending on the pitch described above, and other factors. For example, the number of microneedles per $cm^2$, of the substrate surface of the microneedle array is generally about 50, to 300,, preferably about 100, to 200, and more preferably about 120, to 160. Although the arrangement of the plurality of microneedles in the microneedle array is not particularly limited, they are preferably arranged in a grid pattern.

In the microneedle array of the present invention, the substrate is not particularly limited, as long as it is a film or sheet on which the microneedles can be attached, held, or formed. The substrate may be a film or sheet having the same composition as the microneedles, or it may be a film or sheet having a different composition from the microneedles. Specific examples of films or sheets having a different composition from the microneedles include films or sheets made of polymethyl methacrylate, cellulose acetate, ethyl cellulose, polyethylene resin, polypropylene resin, ethylene-propylene copolymer, ethylene-vinyl acetate copolymer, vinyl chloride-based resin, vinylidene chloride resin, vinyl acetate-vinyl chloride copolymer, polyamide-based resin, polyester resin, acrylonitrile-butadiene-styrene copolymer, styrene-isoprene-styrene copolymer, styrene-ethylene-butylene-styrene copolymer, urethane resin, silicon resin, aluminum, etc. In terms of the ease of production, the substrate is preferably formed of a film or sheet having the same composition as the microneedles. In this case, the substrate can be integrally formed with the microneedles.

The substrate is not particularly limited; however, it is preferable that the microneedles can be attached or held on the surface of the substrate, and that the substrate has a thickness that allows the microneedles to be inserted into the surface layer and/or stratum corneum. Although the thickness of the substrate may be generally determined within the range of about 50 µ, m or more, for example, the thickness is preferably about 50, to 500 µ, m, and more preferably about 80, to 300 µ, m, further more preferably about 100, to 200 µ, m.

The method of producing the microneedle array of the present invention is not particularly limited, and the microneedle array can be produced by a known method. Examples of the microneedle array production method of the present invention include methods (i) and (ii) described below.

(i) An aqueous solution in which components for forming the microneedles are dissolved is poured into a mold in which the form of a microneedle array is recessed, so that a microneedle part and a substrate part are formed. The moisture is evaporated, and the resultant is dried at room temperature or by heating. Then, the formed microneedle array is removed from the mold. According to this method, a microneedle array whose microneedles and substrate have the same composition can be produced.

(ii) An aqueous solution in which components for forming the microneedles are dissolved is poured into a mold in which the form of a microneedle array is recessed. The moisture is evaporated, and the resultant is dried at room temperature or by heating. Subsequently, a substrate is laminated on the microneedles formed above, and the bottom of the microneedles and the substrate are bonded or combined with each other. The microneedles are then removed, together with the substrate, from the mold. According to this method, a microneedle array whose microneedles and substrate have different compositions can be produced.

In the above methods (i) and (ii), the aqueous solution in which components for forming the microneedles are dissolved is not particularly limited as long as it has a concentration sufficient enough to enable proteoglycan to dissolve. For example, an aqueous solution having a proteoglycan concentration of about 1, to 30, wt. %, preferably about 1, to 25, wt. % can be used.

The microneedle array of the present invention is used by applying it to the skin so that the microneedles are inserted into the skin surface layer and/or stratum corneum. More specifically, the microneedle array of the present invention is attached to the skin so that the microneedles are inserted into the skin surface layer and/or stratum corneum, and the microneedle array is left in this state. Thereby, proteoglycan in the microneedles dissolves in the body because of the subcutaneous temperature and moisture and is eluted under the skin and underlying tissues to exert useful pharmacological activity based on the proteoglycan. When microneedles contain water-soluble polymers or cosmetically or pharmaceutically acceptable medicinal components, as described above, these components in the microneedles are eluted into the skin, together with the proteoglycan, so that useful pharmacological activity based on the proteoglycan and these components is exerted under the skin.

In order to more effectively achieve the pharmacological activity of the proteoglycan, etc., it is preferable that the microneedles inserted into the skin surface layer and/or stratum corneum are held as they are for generally about 30, minutes or more, preferably 30, to 300, minutes, and preferably about 60, to 180, minutes. This allows the proteoglycan forming the microneedles to sufficiently dissolve and elute under the skin.

As described above, the microneedle array of the present invention can supply at least proteoglycan into the skin and underlying tissues, and is thus used for cosmetic or medical applications that take advantage of the proteoglycan activity.

For example, proteoglycan is known to exhibit promotion of epidermal cell growth (Non-patent Document 1). Hence, the microneedle array of the present invention can be used for cosmetic purposes, such as skin whitening, moisturizing, and antiaging based on the proteoglycan action.

Proteoglycan is also known to exhibit actions of immunostimulation, anti-inflammation, etc. Accordingly, the microneedle array of the present invention is also effective for medical purposes, such as skin tissue immunological adjuvants, antiphlogistics for inflammation of skin tissue, etc.

EXAMPLES

The present invention is described in detail below with reference to Examples. However, the present invention should not be interpreted as being limited to the Examples. The proteoglycan used in the following Examples was chondroitin sulfate proteoglycan derived from salmon nasal cartilage (eluted from salmon nasal cartilage using acetic acid; produced by Kakuhiro Corporation, Japan).

Example 1

Production of Microneedle Array

An aqueous solution containing 20, wt. % of proteoglycan was poured into a mold in which the form of a microneedle array was recessed. FIG. 1 shows a cross-sectional view of the mold (1) in which the form of a microneedle array was recessed and the 20, wt. % proteoglycan-containing aqueous solution (2) was poured. More specifically, Sign 1 in FIG. 1 indicates a mold in which concave portions (11) for forming microneedles are formed in such a manner that a pattern of microneedles in a predetermined shape is formed on the surface of a photopolymer by a lithography technique (light irradiation), followed by electroforming to transfer the pattern of the microneedles in the predetermined shape. The concave portions (11) for forming microneedles shown in FIG. 1 each have a concave portion in the form of a konide-like shape having an open end diameter (corresponding to the root diameter of the microneedle) of 200 µ, m, a bottom diameter (corresponding to the tip diameter of the microneedle) of 40 µ, m, and a depth (corresponding to the length of the microneedle) of 800 µ, m. The concave portions are arranged in a grid pattern at intervals of 800 µ, m on the photopolymer, and 144 concave portions are formed per $cm^2$.

Sign 2 in FIG. 1 indicates an aqueous solution layer formed by pouring the 20, wt. % proteoglycan-containing aqueous solution into the mold (1).

The 20, wt. % proteoglycan-containing aqueous solution poured into the mold (1) was dried in this state in an oven at 35°, C. for 5, hours to evaporate the moisture. The dried product formed on the mold (1) was then removed from the mold (1). The microneedle array of the present invention shown in FIG. 2 was obtained in this manner. In the microneedle array, a number of fine solid konide-like shape microneedles (4) are formed on the surface of the substrate (3) by pouring the 20, wt. % proteoglycan-containing aqueous solution into the concave portions (11) for forming microneedles, followed by drying. The substrate (3) and microneedles (4) are both composed of proteoglycan. The produced microneedle array is in the shape of an ellipse with a size of 6, mm (shorter axis) x 10, mm (longer axis), depending on the size of the substrate (3).

The microneedles (4) are each in a solid konide-like shape with a length (Sign a) of 800, μm, a root diameter (Sign b) of 200, μm, and a tip diameter (Sign c) of 40, μm; and the distance (Sign d) between the tip of one microneedle (4) and the tip of another adjacent microneedle (4) is 800, μm. The microneedles (4) are arranged on the substrate in a grid pattern at the above intervals, and about 144, microneedles are formed per $cm^2$. The thickness (Sign e) of the substrate (3) is 200, μm.

The microneedles of the thus-produced microneedle array were fine needles, had good strength and flexibility, and could be inserted into the skin surface layer and/or stratum corneum with almost no pain, as described above. Moreover, the microneedles, which were composed only of proteoglycan except for residual moisture, exhibited excellent solubility under the skin by maintaining them under the skin for about 90, minutes after subcutaneous insertion.

Additionally, the microneedle array having microneedles composed of 100% proteoglycan except for residual moisture, as described above, is expected to be effective for cosmetic or medical purposes based on proteoglycan activity. The microneedle array is also expected to be effective for cosmetic purposes, such as wrinkle smoothing, based on proteoglycan activity.

Although the microneedle array produced in Example 1, comprises konide-like shape microneedles, a microneedle array comprising circular truncated cone-shape microneedles can be produced by using concave portions (11) for forming microneedles in the form of a circular truncated cone.

Example 2

Usability Assessment of Microneedle Array

Using an aqueous solution containing 20, wt. % of proteoglycan and 10, wt. % of Evans blue dye, a microneedle array in the shape of an ellipse with a size of 8, mm (shorter axis)×10, mm (longer axis) (length of microneedle: 800 82, m) was produced in the same manner as in Example 1. The produced microneedle array was cut into pieces about 7, mm in size, and they were applied to the knees of rats to examine how the Evans blue dye penetrated into the surrounding tissue of the knees.

(1) Test Animals

SD rats (Crl:CD, male, 5, weeks old, 164, to 183 g; Charles River Laboratories Japan, Inc.) were kept overnight (lighting hours: 12, hours, non-lighting hours: 12, hours) under the conditions in which the temperature was 23±2°, C., and the humidity was 60±10%. They were then subjected to the following experiments. The test animals were treated in accordance with the guidelines for animal experiments of Otsuka Pharmaceutical Co., Ltd., and they were allowed to freely take food (ME: Oriental Yeast Co., Ltd.) and water (tap water).

(2) Test Method

The hair of both knees of the individual test animals (n=5) was shaved with an electric shaver and then removed with a depilatory cream. The microneedle arrays (about 7, mm×7, mm) produced above were applied to the dehaired skin of the knees. More specifically, the microneedle array was pressed and applied to the skin of the knee so that the microneedles were inserted into the skin, and the microneedle array was press-fixed to the skin by taping. The microneedle arrays were applied to the test animals in this manner, and the test animals were secured in Bollman restraining cages to prevent movement.

After two hours from the application of the microneedle arrays, the test animals were released from the cages, and euthanized under ether anesthesia. Thereafter, the microneedle arrays were removed from the skin, and the form of the microneedles, the surface and subcutaneous tissue of the skin of the knees to which the microneedle arrays were applied were observed to evaluate the solubility of the microneedles under the skin and the penetrance of Evans blue dye staining in the skin surface and subcutaneous tissue.

(3) Test Results (3-1) Form of Microneedle

The 800-μm microneedle portions of the applied microneedle array all disappeared. This confirmed that the microneedles inserted into the skin subcutaneously dissolved because of the body temperature and the surrounding moisture.

(3-2) Observation of Microneedle Array-Applied Site (Knee)

In all the test animals (n=5), the surface and subcutaneous tissue of the skin of the microneedle array-applied site were stained by the Evans blue dye, while the muscular layer was not stained. This confirmed that the components (proteoglycan and Evans blue dye) eluted by dissolution of the microneedles reached under the skin. Additionally, no abnormal findings (e.g., bleeding) were observed in the microneedle array-applied sites (skin, subcutaneous tissue, and muscular layer) of the test animals.

The invention claimed is:

1. A microneedle array comprising one or more microneedles formed on a surface of a substrate, the microneedles comprising proteoglycan as a base material, wherein:
   each of the microneedles is a solid needle,
   each of the microneedles has a konide-like shape or a circular truncated cone shape,
   the proteoglycan content in each of the microneedles is 50, to 100, wt.%,
   the proteoglycan is distributed homogeneously in the solid needles, and
   the proteoglycan is chondroitin sulfate proteoglycan.

2. The microneedle array according to claim 1, wherein each of the microneedles has a root diameter of 120, to 400 μ, m, a tip diameter of 5, to 100 μ, m, and a length of 100, to 5000 μ, m, and a distance between tips of adjacent microneedles is 100, to 1800 μm.

3. The microneedle array according to claim 1, wherein the proteoglycan is derived from fish.

4. The microneedle array according to claim 3, wherein the fish is salmon, shark or jellyfish.

5. The microneedle array according to claim 1, wherein each of the microneedles contains, in addition to the proteoglycan, a water-soluble polymer other than proteoglycan, or a cosmetically or pharmaceutically acceptable medicinal component.

6. The microneedle array according to claim 1, wherein the substrate has the same composition as the microneedles.

* * * * *